United States Patent
Richardson (10) Patent No.: US 7,262,419 B2
(45) Date of Patent: Aug. 28, 2007

(54) FLUORESCENCE ABSORPTION MICROSCOPY

(75) Inventor: Timothy M. Richardson, Bolton (CA)

(73) Assignee: 1192062 Alberta Ltd., Calgary (CA)

( * ) Notice: Subject to any disclaimer, the term of this patent is extended or adjusted under 35 U.S.C. 154(b) by 165 days.

(21) Appl. No.: 11/122,238

(22) Filed: May 5, 2005

(65) Prior Publication Data
US 2007/0057199 A1 Mar. 15, 2007

Related U.S. Application Data

(60) Provisional application No. 60/567,822, filed on May 5, 2004.

(51) Int. Cl.
*G01N 21/64* (2006.01)
(52) U.S. Cl. .................................. 250/458.1
(58) Field of Classification Search ............. 250/458.1
See application file for complete search history.

(56) References Cited

U.S. PATENT DOCUMENTS 4,773,097 A * 9/1988 Suzaki et al. ............... 382/128
5,760,406 A * 6/1998 Powers .................... 250/461.2

FOREIGN PATENT DOCUMENTS

WO    WO98/45744 A2   10/1998

* cited by examiner

*Primary Examiner*—Constantine Hannaher (57) ABSTRACT

A microscopy technique for viewing regions where a sample absorbs, as opposed to emits, fluorescent light. The technique includes illuminating a sample with an exciter light in order to generate fluorescent light from the sample and filtering light received from the sample such that fluorescent light is substantially attenuated. Regions that primarily emit fluorescent light will then be black, but regions where the exciter is primarily absorbed but where there is little emissive fluorescent activity can be viewed as a darker shade of the background color.

13 Claims, 7 Drawing Sheets

Legends added

FLUORESCENCE ABSORPTION MICROSCOPY

RELATED APPLICATIONS

This application claims the benefit of priority of U.S. Provisional Patent Application Ser. No. 60/567,822 filed May 5, 2005.

FIELD OF INVENTION

The invention generally relates to the field of microscopy, and more specifically to fluorescent contrast techniques and related apparatus.

BACKGROUND OF INVENTION

An important class of microscopy image contrast techniques is based on the phenomenon of photoluminescence. It well known that when certain molecules are exposed to an exciter light (typically a high power, short wave ultra-violet or blue light), they will emit a longer wavelength light (i.e., fluorescent light). Fluorescence (and/or phosphorescence) may occur naturally in a sample, for example, chlorophyll in botanical specimens, or may be induced through the use of particular binding agents such as dyes or other such fluorochromes. In conventional fluorescence microscopy, an excitation filter is typically employed to generate the exciter light from a polychromatic illumination source, and a sharp barrier or emission filter is typically employed to permit only the fluorescent light to reach the ocular or camera (i.e., the viewer). Thus, for example, a short-wave blue light exciter filter in conjunction with a red barrier filter enables chlorophyll-containing organelles to appear brilliant red over a relatively dark background.

One of the shortcomings with conventional fluorescence microscopy, however, is that the information which is provided to the viewer only indicates the area or region where fluorescent light is emitted from the sample. The conventional technique does not inform the viewer as to where the light is absorbed, which may be different from where light is emitted. This difference may arise, for example, due to some type of tunneling mechanism or other unexplained phenomenon.

Accordingly, it would be desirable to be able to image a sample in order to ascertain where the exciter light is being absorbed, and to ascertain if fluorescent emitting structure is or is not co-located with the fluorescent absorbing structure. This would enable the microscopist to determine if the sample does indeed exhibit some type of tunneling effect.

SUMMARY OF INVENTION

A first aspect of the invention relates to a method and related apparatus for viewing the absorption of a fluorescent exciter light. According to this aspect of the invention an image is acquired by illuminating a sample with an excitation light so as to generate fluorescent light from the sample. The light received from the sample is filtered such that the fluorescent light emitted by the sample is substantially attenuated, thereby acquiring a filtered image of the sample. The filtered image is provided as an observable image to a viewer, e.g., a person or an automated vision processing system. The observable image visually indicates areas where the exciter light is predominantly absorbed.

The light illuminating the sample preferably consists essentially of wavelengths which generate fluorescence in the sample. Preferably, substantially all light received from the sample is filtered except for the exciter light.

Another aspect of the invention relates to a method and related apparatus for differentially comparing a fluorescent image with a fluorescent absorption image. According to this aspect of the invention an image is acquired by illuminating a sample with an exciter light in order to generate fluorescent light from the sample. A first image of the sample is acquired by substantially attenuating the fluorescent light received from the sample. A second image of the sample is acquired by substantially attenuating the exciter light received from or otherwise reflected off the sample. The first image is differentially compared against the second image and displayed to a viewer (e.g., a person or an automated vision processing system). For example, the differential image can be the result of a differential matrix calculation such as $I_i = |A_i - \overline{B}_i|$, where $A_i$ represents a pixel from the first image, $B_i$ represent the corresponding (i.e., similarly situated) pixel from the second image, and $\overline{B}_i$ is the inversion thereof. (In this example, each pixel is a 24 bit value comprising three discrete 8-bit integers, each integer representing one of the primary colors.)

BRIEF DESCRIPTION OF DRAWINGS

The foregoing and other aspects of the invention will be better understood with reference to a detailed description of preferred embodiments of the invention, discussed below, in conjunction with the drawings, wherein.

DETAILED DESCRIPTION OF PREFERRED EMBODIMENTS

Figure 1:
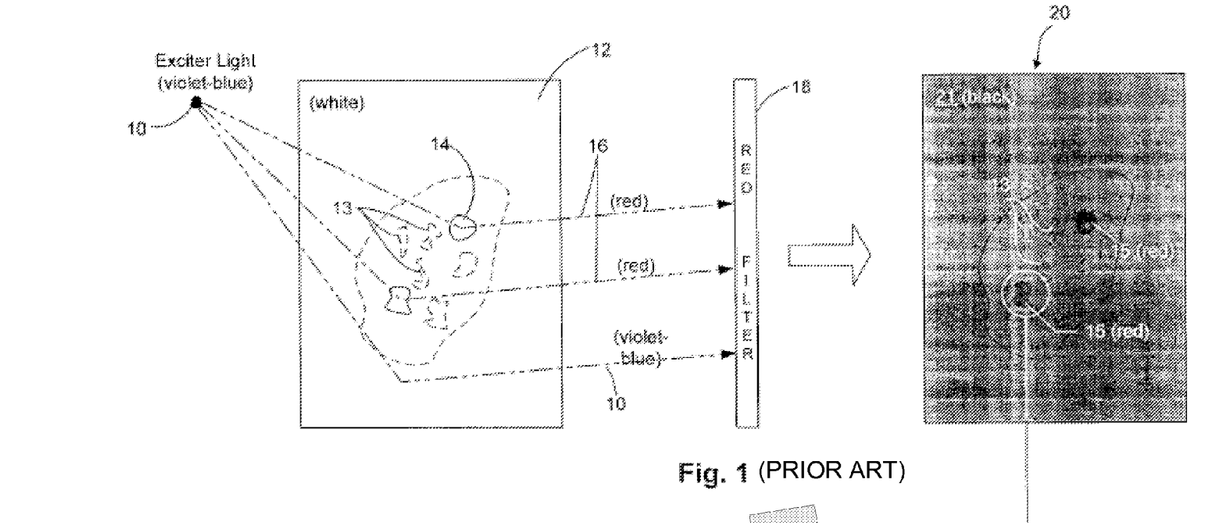
FIG. 1 diagrammatically illustrates conventional fluorescence microscopy techniques and the images resulting therefrom.
Figure 1A:
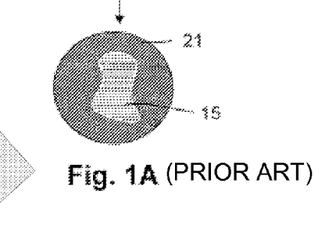
FIG. 1A is a color-schematic detail view of a portion of FIG. 1 (wherein colors are schematically represented by different cross-hatching patterns as indicated in FIG. 4)

FIG. 1 schematically illustrates the conventional fluorescence microscopy technique wherein an exciter light 10 (blue, in this example) is used to illuminate a sample 12. Amongst other structures 13, the sample 12 includes structure 14 which emit fluorescent light 16 (red, in this example). All light acquired from the sample which forms the basis for an image of the sample displayed to an observer is filtered by an emission filter 18 having a pass band tuned to the wavelengths of the expected fluorescent light, which in this case is a red filter. Consequently, the resultant image 20 of the sample viewed by the observer shows only the fluorescent regions 15 in the fluorescent color, e.g., red 2. The background 21 of the resultant image 20 will be dark or black and, depending on the illumination technique employed and the spectrum of emitted light, the other structure 13 will generally not be visible or will be poorly visible. This is difficult to see in the black and white patent drawings but is shown schematically in the detail view of FIG. 1A. As previously indicated, one of the shortcomings with the foregoing technique is that it enables the observer to view only the regions where the fluorescent light is being emitted, which may or may not correspond to regions where the exciter light 10 is absorbed.

Figure 2:
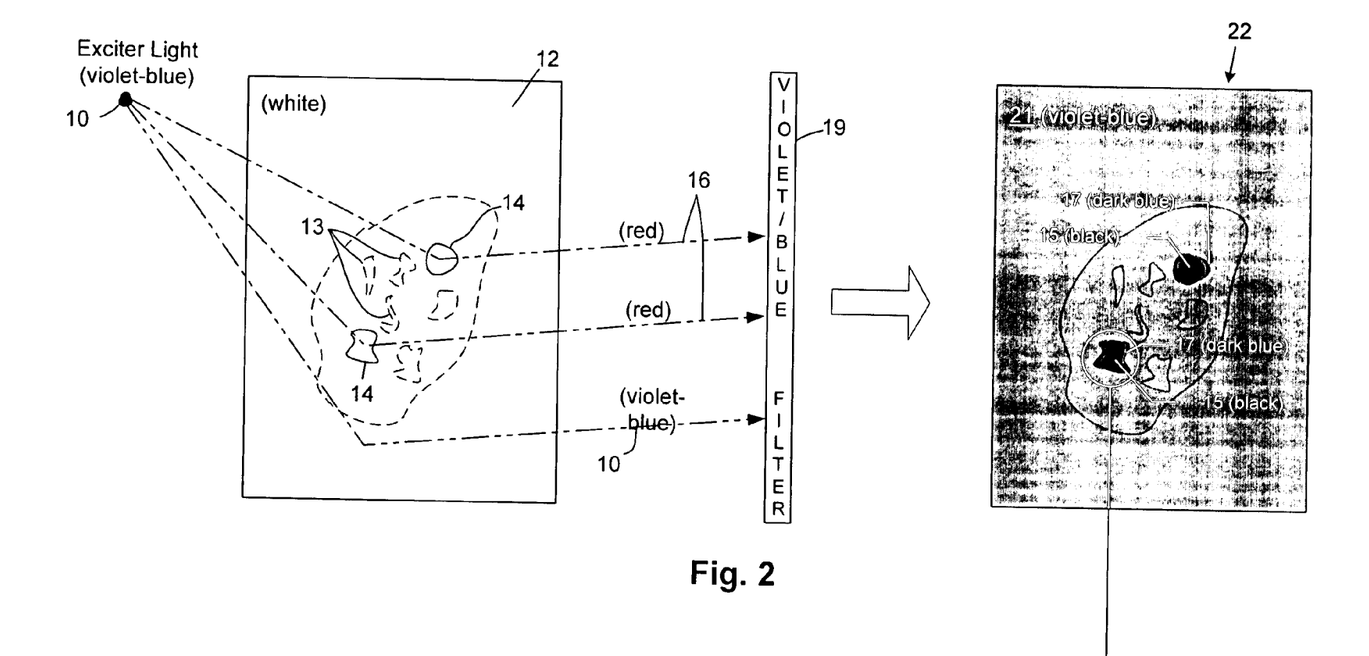
FIG. 2 diagrammatically illustrates the technique of fluorescence absorption microscopy according to a preferred embodiment of the invention and the images resulting therefrom.

FIG. 2 schematically illustrates fluorescence absorption microscopy according to one embodiment of the invention. In the preferred technique, an exciter light 10 is used to illuminate the sample 12, which will emit fluorescent light 16. All light acquired from the sample which forms the basis of an image of the sample for display to an observer is filtered by an emission filter 19. In contrast to the prior art, the emission filter 19 substantially attenuates the wavelengths of the expected fluorescent light. Consequently, the resultant image 22 of the sample viewed by the observer will be black in regions where the fluorescent light is predominantly emitted.

Figure 2A:
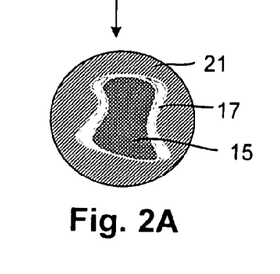
FIG. 2A is a color-schematic detail view of a portion of FIG. 2.

In preferred embodiments, the emission filter 19 has a pass band, which allows through the wavelengths of the exciter light as reflected off of the sample. In most cases, the pass band of the emission filter 19 will be tuned to the wavelengths of the exciter light because the reflected light will be the same color as the exciter light, particularly if the sample is substantially transparent and/or is disposed over a whitish background. If desired, the emission filter 19 can be constructed to substantially attenuate potentially harmful ultra-violet light and pass through only the visible component of the exciter light. Thus, for example, filter 19 can be a violet-blue filter. Consequently, as exemplified in FIG. 2, the background color 21 of the resultant image 22 will be the (visible) color of the exciter light 10, e.g., violet-blue, and the fluorescent regions 15 will be black. However, in regions 17 where the exciter light is primarily absorbed but where little fluorescent activity exists, such regions will be viewable as a darker shade of the background color, e.g., a dark blue. This is difficult to see in the black and white patent drawings, but is shown schematically in the detail view of FIG. 2A.

Figure 3:
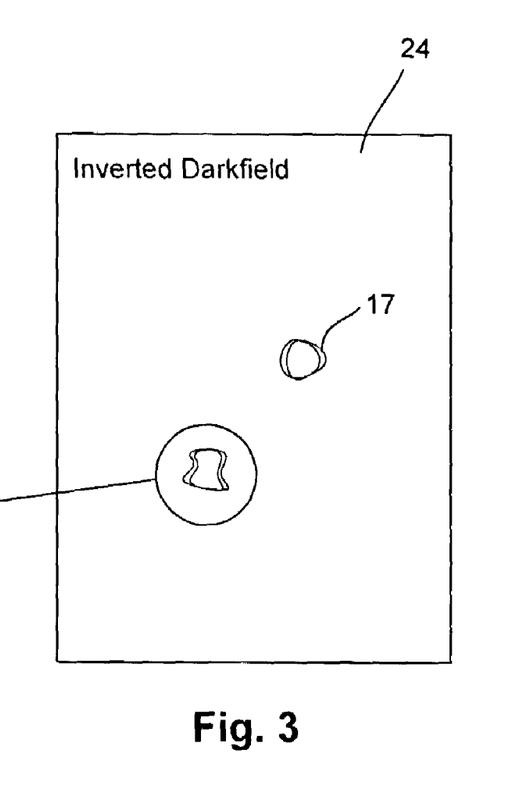
FIG. 3 is a diagram of an electrically inverted, fluorescence-absorption image acquired using a darkfield illumination system.
Figure 3A:
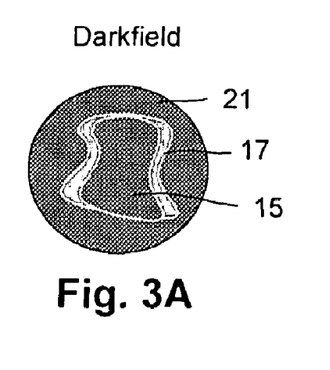
FIG. 3A is a color-schematic detail view of a portion of FIG. 3, prior to inversion.
Figure 3B:
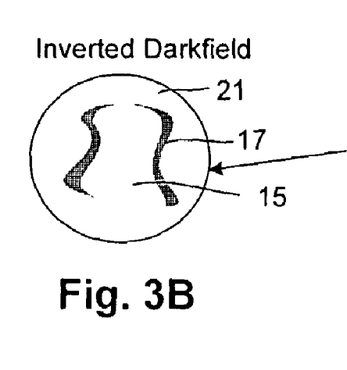
FIG. 3B is a color-schematic detail view of the same portion of FIG. 3, post inversion.
Figure 4:
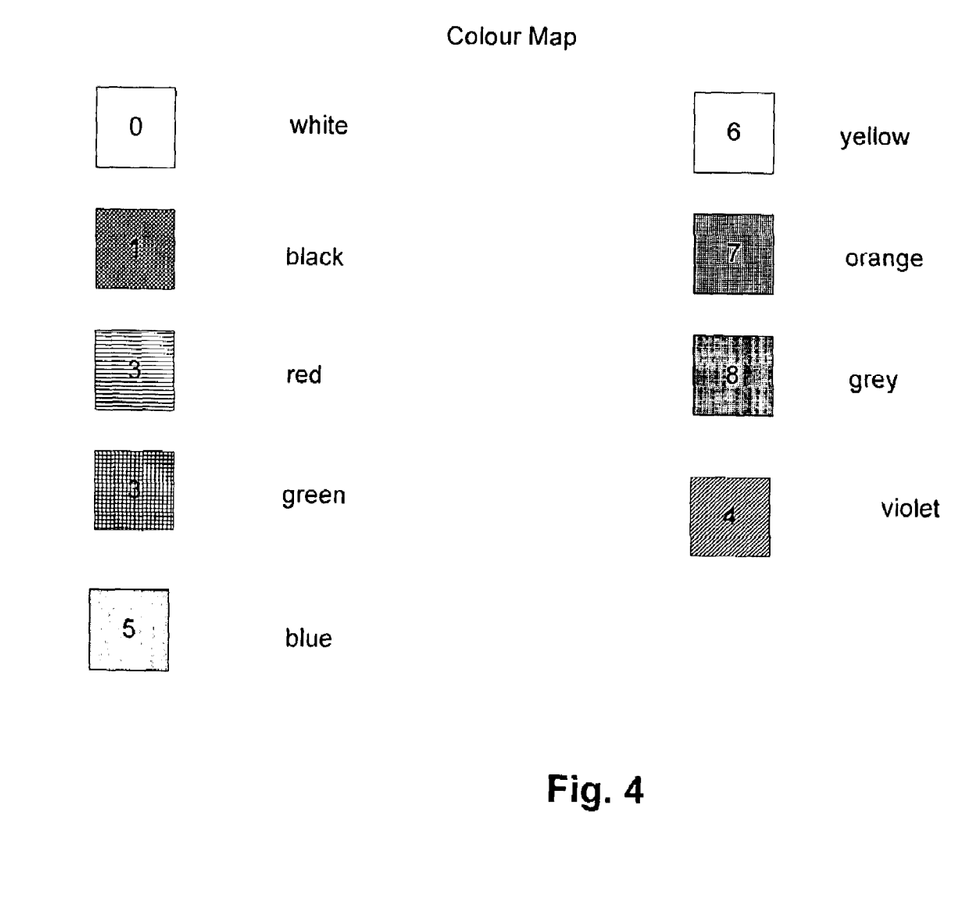
FIG. 4 is a concordance map that correlates various types of cross-hatching patterns employed in the drawings with representative colors.

The contrast between the predominantly absorbing regions 17 of the sample and the background color 21 may possibly be significantly improved by employing dark field illumination techniques, as known in the art per se. In this case, as schematically illustrated in the detail view of FIG. 3A, the background color 21 is black. The predominantly absorbing region 17 of the sample is dark blue and the fluorescing region(s) 15 is black. By inverting the colors of the sample image, the background and fluorescent regions 21, 15 of the image can be made to substantially disappear, leaving the emphasis on the predominantly-absorbing regions 17 in the resultant image 24, as seen in FIG. 3. In the foregoing example, regions 17 will assume an orange color when inverted, as schematically illustrated in FIG. 3B.

Figures 5, 5A:
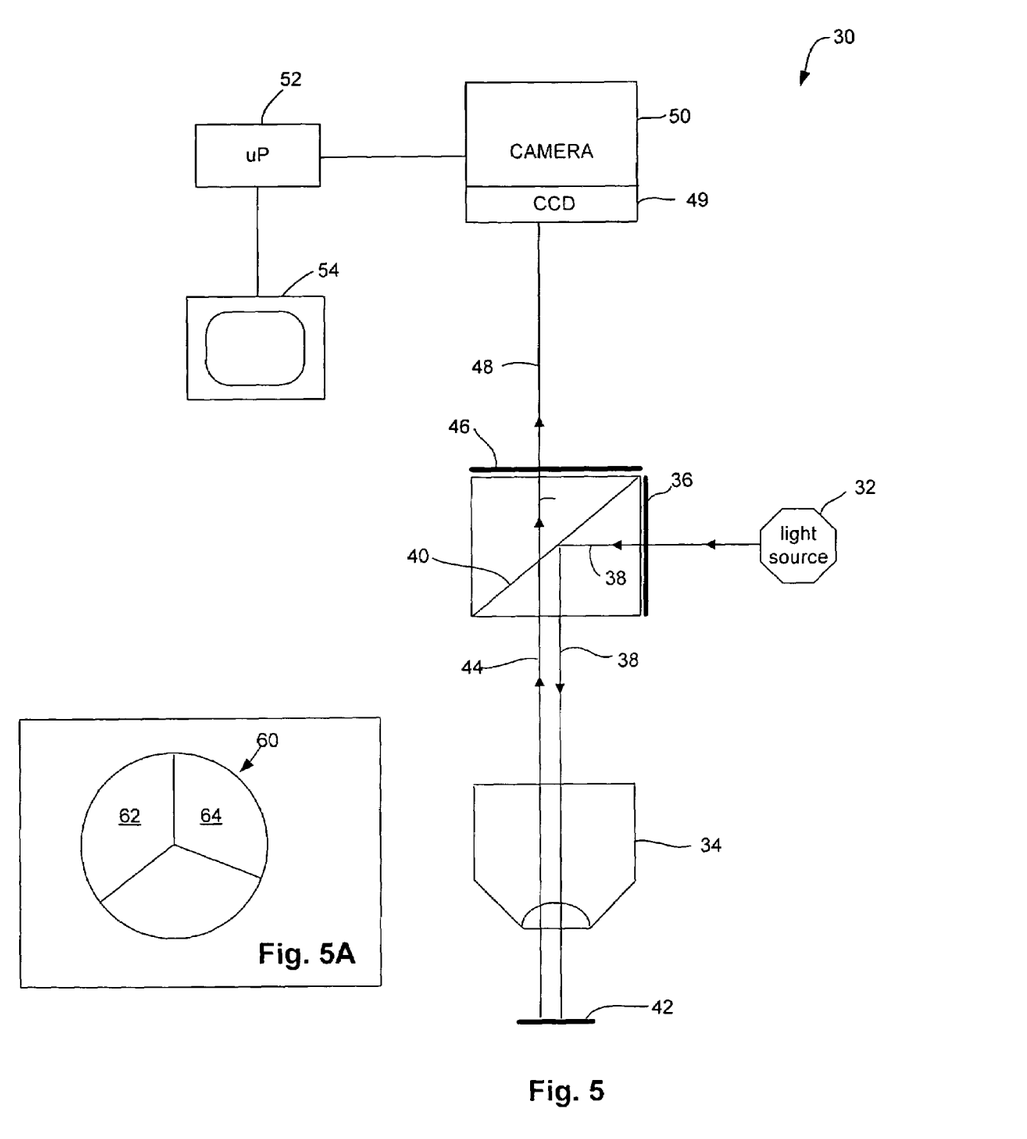
FIG. 5 is a schematic diagram of an epi-fluorescent microscope according to the preferred embodiment.

FIG. 5 schematically illustrates the basic components of a microscope 30 configured to provide fluorescence absorption microscopy as discussed above. The illustrated embodiment is an epi-flourescent microscope wherein the objective 34 acts as the condenser for the exciter light and as an objective for the fluorescent light. Light source 32 is preferably a strong polychromatic illumination source, which is filtered by an excitation filter 36 to provide the desired spectrum for exciter light 38. For example, a high-pressure xenon arc can be utilized as the light source 32 in order to provide a high intensity UV light. Monochromatic light sources such as lasers can also be employed in the alternative. A color splitter or dichroic mirror 40 reflects the exciter light 38 through the objective 34 to illuminate the sample specimen on stage 42. Fluorescent light 44 generated by the specimen and the reflected background light is collected by the objective 34 and passes through the dichroic mirror 40 and an emission filter 46. As discussed previously, the emission filter 46 preferably attenuates the wavelengths of the expected fluorescent light, and passes through the visible portion of the exciter light 48. In the illustrated embodiment, the filtered light 48 impinges upon a CCD sensor 49 of a digital camera 50, although in alternative embodiments the filtered light 48 can be viewed through an ocular. A microprocessor 52 is coupled to the camera 50 and a display monitor 54 in order to display the resultant image. The microprocessor provides the ability to easily manipulate the resultant digital image, such as providing a color inversion function.

In the preferred embodiment, the excitation and emission filters 36, 46 are mounted on wheels (not shown), which enable the microscopist to vary the particular filter used. This can be carried out manually, or more preferably under computer control. See in this regard PCT Publication No. WO 98/45744, "Color Translating UV Microscope", the contents of which are incorporated by reference herein, for a description of computer-controlled rotating filters. By varying the filters, it is possible to provide a two or three-segment emission filter 60, as shown in FIG. 5A. A first filter segment 62 has its passband keyed to pass through fluorescent light and block the excitation light as in the prior art. This provides a conventional resultant fluorescent image as shown in FIG. 1. A second filter segment 64 substantially attenuates the fluorescent light and passes through the visible portion of the excitation light. This provides a resultant fluorescent absorption image such as shown in FIG. 2. These first and second images can be simultaneously displayed on the monitor 54 for comparison. Alternatively, the one image can be overlaid over the other image for display. For example, the microprocessor 52 can carry out a differential matrix calculation such as $I_i = |A_i - \overline{B}_i|$, where $A_i$ represents a pixel from the first image, $B_i$ represents the corresponding (i.e., similarly situated) pixel from the second image, and $\overline{B}_i$ is the inversion thereof. (In this example, each pixel is a 24 bit value comprising three discrete 8-bit integers, each integer representing one of the primary colors.) The image resulting from this calculation highlights the difference between the first and second images. The microprocessor can carry out other types of differential processing calculations such as edge detection algorithms as known in the art per se. These comparisons can be carried out cyclically at a frame rate of 1/30 second or close thereto, providing the microscopist with substantially real time differential images. The differential comparison of a conventional fluorescent image against a fluorescent absorption image is particularly useful if the latter does not readily differentiate between the predominantly absorbing regions and the fluorescing regions. However, the differences between the two regions will likely be highlighted in the differential image.

Figure 6:
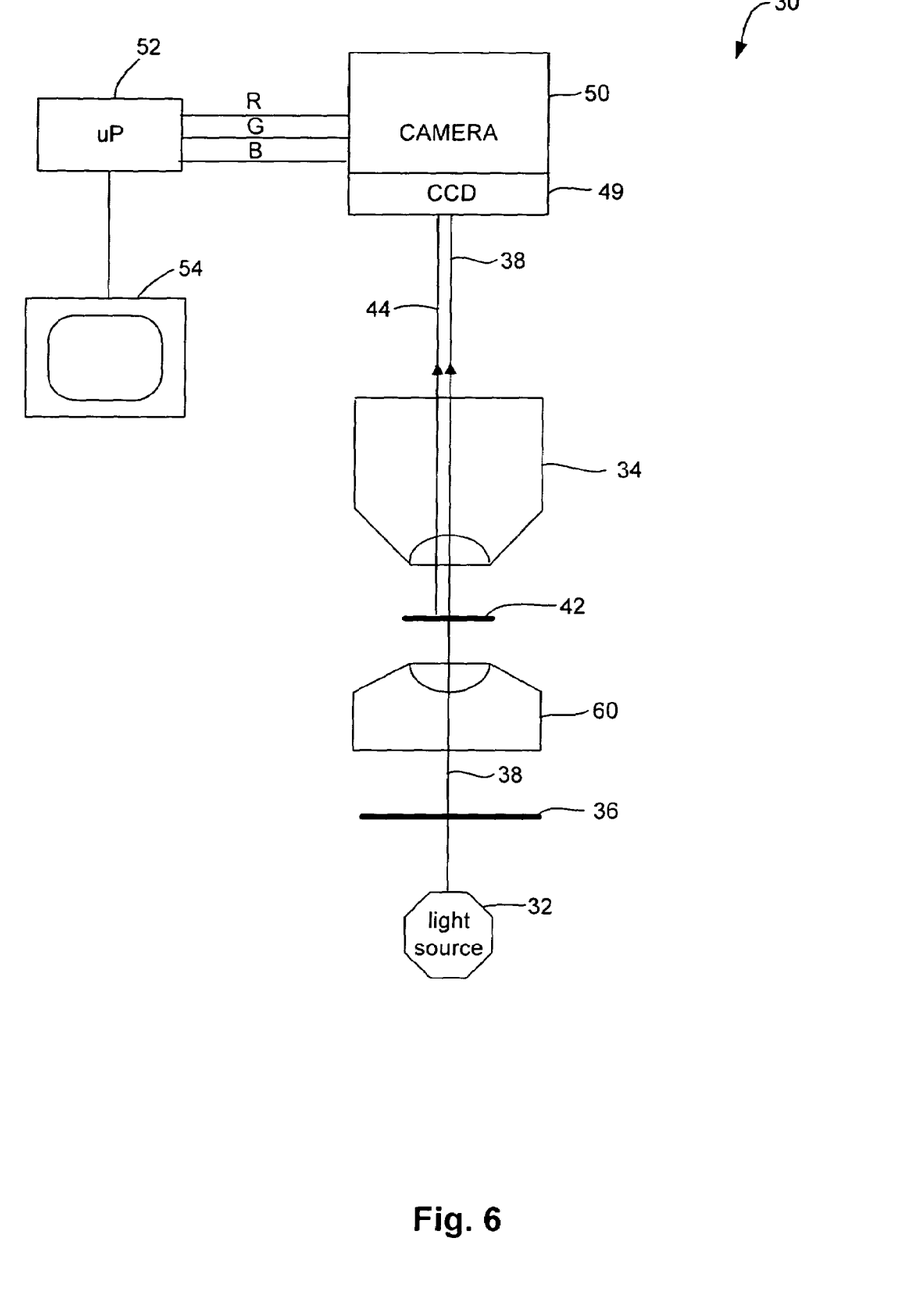
FIG. 6 is a schematic diagram of a transmitted fluorescent microscope according to an alternative embodiment.

An alternative embodiment, which may eliminate the need for the emission filter, is shown in FIG. 6. This microscope has a transmitted light illumination system wherein the exciter light 38, generated by light source 32 and excitation filter 36, is collected by a condenser 60 to illuminate a specimen on stage 42. The exciter light and fluorescent light generated thereby are collected by objective 34 to impinge upon the CCD sensor 49. The CCD camera provides three output color channels or planes, e.g., red, green and blue. The CCD sensor is sensitive to the visible spectrum and thus substantially attenuates UV information. However, the blue plane is sensitive to the visible component of the exciter light and insensitive to other colors. If the microprocessor is programmed to display only the blue color plane, the camera essentially functions as a blue-violet emission filter and thus can provide a fluorescence absorption image such as shown in FIG. 2. Similarly, the fluorescent light, which has a longer wavelength than the exciter light, will be predominantly centered in either red or green, or a combination of both. If the microprocessor is programmed to display only one (or both) of these planes, the camera essentially functions as a red (or red/green) filter and thus can provide a conventional fluorescent image such as shown in FIG. 1. Having acquired the conventional fluorescent image and the fluorescent absorption image, the microprocessor can also be programmed to display a comparison or differential of the two images. For example, the monitor can be programmed to display $I_i=|R_i-\overline{B}_i|$, where $R_i$ represents a pixel from the red plane, $B_i$ represent the corresponding pixel from the blue plane, and $\overline{B}_i$ is the inversion thereof.

Figure 7:
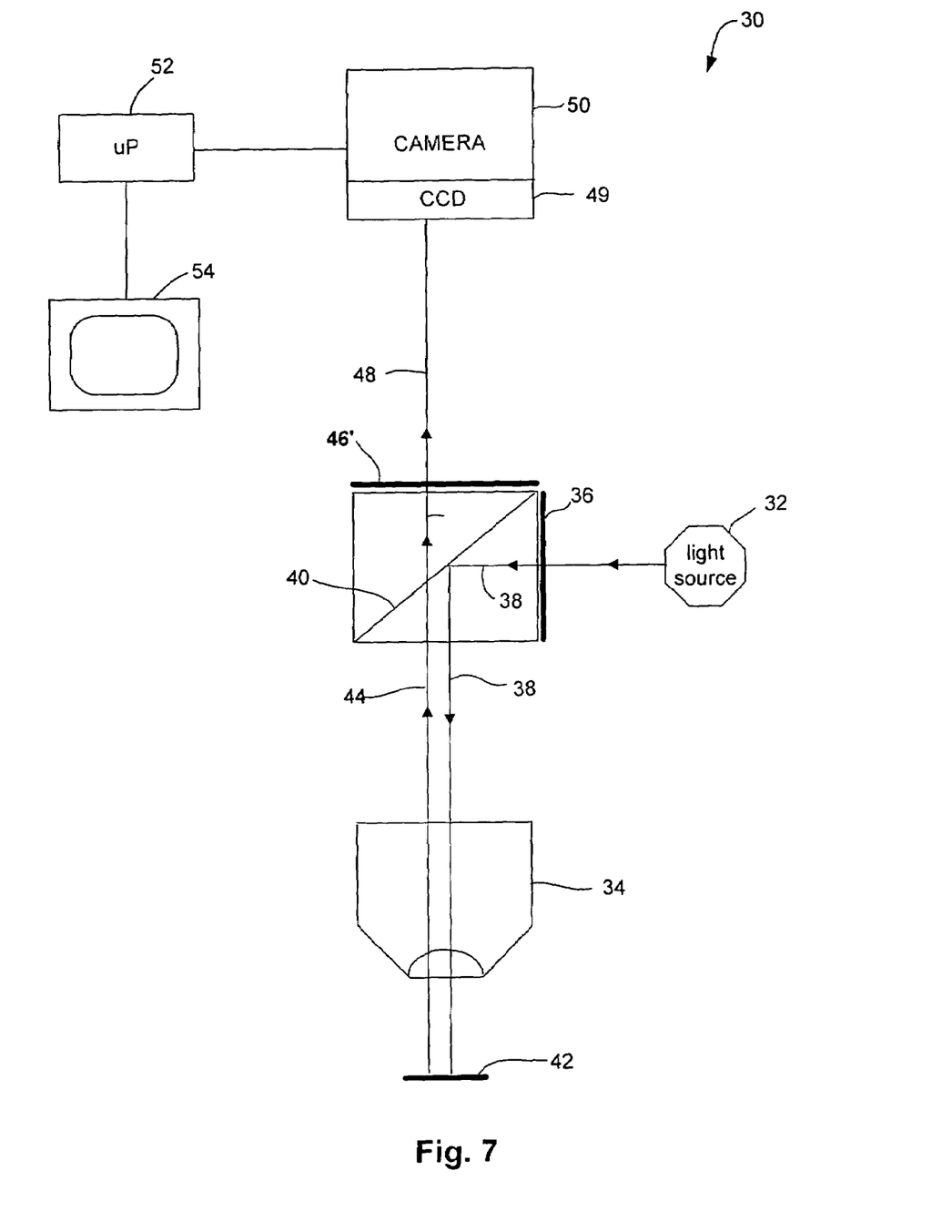
FIG. 7 is a schematic diagram of an epi-fluorescent microscope according to an alternative embodiment.

FIG. 7 shows an alternative embodiment of a microscope which optically enables the fluorescent absorption image to be viewed in conjunction with the conventional fluorescent image. This microscope is substantially similar to the epi-illumination microscope shown in FIG. 5. However, filter 46' has a passband designed to permit through fluorescent light as well as significant leakage of the excitation wavelength (or at least the visible part thereof). In this case, depending in part on the strength of the fluorescing light, the primarily absorbing regions should be visible as a darker shade of the reflected background exciter light.

While the preferred embodiment has been shown using an epi-illumination system, those skilled in the art will understand that the techniques of fluorescence absorption microscopy and differential fluorescence absorption microscopy can also be applied, inter alias, to transmitted light, darkfield, or confocal illumination systems. Similarly, those skilled in the art will appreciate that a variety of other modification may be made to the methods and apparatus described herein without departing from the spirit of the invention.

The invention claimed is:

1. A microscopy imaging method, comprising:
   illuminating a sample with an exciter light consisting essentially of excitation wavelenghths in order to generate fluorescent light from the sample;
   filtering substantially all light received from the sample, except for the exciter light such that fluorescent light is substantially attenuated, thereby acquiring a filtered image of said sample; and
   inverting the chrominance and luminance of the acquired filtered image and presenting the inverted filtered image for view.

2. A microscopy imaging method comprising:
   illuminating a sample with an exciter light consisting essentially of excitation wavelengths in order to generate fluorescent light from the sample;
   filtering substantially all light received from the sample, except for the exciter light, such that fluorescent light is substantially attenuated, thereby acquiring a filtered image of said sample; and
   inverting the chrominance but not the luminance of the acquired filtered image and presenting the inverted image for view.

3. A microscopy imaging method, comprising:
   illuminating a sample with an exciter light consisting essentially of excitation wavelenghths in order to generate fluorescent light from the sample;
   filtering substantially all light received from the sample, except for the exciter light, such that fluorescent light is substantially attenuated, thereby acquiring a filtered image of said sample; and
   inverting the luminance but not the chrominance of the acquired filtered image and presenting the inverted image for view.

4. A microscopy imaging method, comprising:
   illuminating a sample with an exciter light in order to generate fluorescent light from the sample;
   acquiring a first image of the sample by substantially attenuating the fluorescent light received from the sample;
   acquiring a second image of the sample by substantially attenuating the exciter light received from or otherwise reflected off the sample;
   obtaining a differential comparison by comparing the first image against the second image wherein the differential comparison is digitally calculated as $I_i=|A_i-\overline{B}_i|$, where $A_i$ represents a pixel from the first image, $B_i$ represents the corresponding pixel from the second image, and $\overline{B}_i$ is the inversion thereof; and
   displaying said comparison for view.

5. A microscopy imaging method according to claim 4, wherein, in acquiring the first image, substantially all light received from the sample is filtered except for the exciter light.

6. A microscope, comprising:
   an illuminator for illuminating a sample with an exciter light in order to generate fluorescent light from the sample;
   a filter for filtering light received from the sample such that fluorescent light is substantially attenuated, the filter filtering substantially all light received from the sample except for the exciter light, thereby acquiring a filtered image of said sample;
   electronic circuitry for inverting the chrominance and luminance of the acquired filtered image; and
   display means for presenting the inverted filtered image for view.

7. A microscope according to claim 6, wherein the light illuminating the sample consists essentially of excitation wavelengths.

8. A microscope, comprising:
   an illuminator for illuminating a sample with an exciter light in order to generate fluorescent light from the sample:
   a filter for filtering light received from the sample such that fluorescent light is substantially attenuated, the filter filtering substantially all light received from the sample except for the exciter light, thereby acquiring a filtered image of said sample;
   electronic circuitry for inverting the chrominance but not the luminance of the acquired filtered image; and
   display means for presenting the inverted filtered image for view.

9. A microscope according to claim 8, wherein the light illuminating the sample consists essentially of excitation wavelengths.

10. A microscope, comprising:
   an illuminator for illuminating a sample with an exciter light in order to generate fluorescent light from the sample;
   a filter for filtering light received from the sample such that fluorescent light is substantially attenuated, the filter filtering substantially all light received from the sample except for the exciter light, thereby acquiring a filtered image of said sample;
   electronic circuitry for inverting the luminance but not the chrominance of the acquired filtered image; and
   display means for presenting the inverted filtered image for view.

11. A microscope according to claim 10, wherein the light illuminating the sample consists essentially of excitation wavelengths.

12. A microscope, comprising:
   an illuminator for illuminating a sample with an exciter light in order to generate fluorescent light from the sample;
   a first filter for substantially attenuating the fluorescent light received from the sample, thereby providing a first image of the sample;
   a second filter for substantially attenuating the exciter light received from or otherwise reflected off the sample, thereby providing a second image of the sample;
   digital means for storing said first and second images;
   a comparator for differentially comparing the first image against the second image to obtain a differential comparison digitally calculated as $I_i = |A_i - \overline{B}_i|$, where $A_i$ represents a pixel from the first image, $B_i$ represent the corresponding pixel from the second image, and $\overline{B}_i$ is the inversion thereof; and
   display means for displaying said comparison for view.

13. A microscope according to claim 12, wherein, in acquiring the first image, said first filter filters substantially all light received from the sample except for the exciter light.

* * * * *